United States Patent [19]

Rei et al.

[11] Patent Number: 5,807,503

[45] Date of Patent: Sep. 15, 1998

[54] LOW TEMPERATURE-STABILIZED ISOTHIAZOLINONE CONCENTRATES

[75] Inventors: Nuno M. Rei, Boxford; Roger G. Hamel, Methuen; Thomas C. McEntee, Topsfield, all of Mass.

[73] Assignee: Morton International, Inc., Chicago, Ill.

[21] Appl. No.: 925,035

[22] Filed: Sep. 8, 1997

[51] Int. Cl.$^6$ .................................................. C09K 15/08
[52] U.S. Cl. ........................................... 252/364; 252/404
[58] Field of Search ...................................... 252/364, 404

[56] References Cited

U.S. PATENT DOCUMENTS

| | | | |
|---|---|---|---|
| 4,086,297 | 4/1978 | Rei et al. | 260/859 PV |
| 4,758,609 | 7/1988 | Rei et al. | 523/122 |
| 5,389,300 | 2/1995 | Schmitt | 252/380 |
| 5,498,344 | 3/1996 | Rei et al. | 252/404 |
| 5,599,827 | 2/1997 | Gironda | 514/372 |

*Primary Examiner*—Paul R. Michl
*Attorney, Agent, or Firm*—Wayne E. Nacker; Gerald K. White

[57] ABSTRACT

A liquid concentrate comprises between about 4 and about 25 wt % of 4,5-dichloro-2-(n-octyl-4-isothiazolin-3-one), between about 25 and about 88 wt % of a plasticizer in which said isothiazolinone compound is soluble and between about 8 and about 50 wt % of benzyl alcohol which stabilizes the concentrate against crystallization and/or freezing at sub-freezing conditions.

7 Claims, No Drawings

LOW TEMPERATURE-STABILIZED ISOTHIAZOLINONE CONCENTRATES

The present invention is directed to liquid concentrates of 4,5-dichloro-2-(n-octyl-4-isothiazolin-3-one) which are stable to crystallization or freezing at sub-freezing temperatures.

BACKGROUND OF THE INVENTION

It is well known to add biocides to thermoplastic resin compositions to protect articles formed from such compositions against microbial degradation. For processing reasons, it is known to provide biocides as concentrates, such as liquid concentrates as taught, for example, in U.S. Pat. No. 4,758,609, or solid concentrates as taught, for example, in U.S. Pat. No. 4,086,297, the teachings of each of which are incorporated herein by reference. Although a number of biocides have been suggested for use in thermoplastic resins, including isothiazolinones, the standard antimicrobial agent in the industry has been and remains 10,10'-oxybisphenoxarsine (OBPA). While OBPA has proven to be a very effective biocide for use in the plastics industry, OBPA may not be optimal for all compounds and processes.

Isothiazolinone compounds are an important family of chemicals with considerable biocidal effectiveness in paint, textiles and metal working fluids. For outdoor weathering applications 4,5-dichloro-2-(n-octyl-4-isothiazolin-3-one) (referred to herein as "DCOIT")shows promise to be a particularly effective biocide in plastics applications. At room temperature DCOIT is in solid form and therefore difficult to handle. DCOIT is more easily handled if dissolved in a liquid carrier, particularly a plasticizer which serves its normal plasticizing function in the end-use plastic composition.

However, even though stable at room temperature (eg 20°–25° C.) plasticizer solutions of DCOIT to freeze when the temperature of the solution becomes cold, as might be encountered during shipping and storage in winter climates. This is highly undesirable as a plastics manufacturer who might receiver frozen concentrate would not only have to thaw the concentrate but take steps to ensure that the DCOIT is fully re-dissolved and that the concentrate is homogeneous.

U.S. Pat. No. 5,498,344, the teachings of which are incorporated herein by reference, discusses this freeze problem and suggests the addition of monoalkylphenols, particularly nonylphenol, to solve the freezing problem. Unfortunately, nonylphenol, the most commercially available of such monoalkylphenols, is becoming increasingly disfavored from an environmental standpoint. Furthermore, nonylphenol is an irritant. Accordingly, it is desired to have more environmentally friendly and safer concentrates of DCOIT which do not freeze under typical low-temperature shipping and storage conditions.

SUMMARY OF THE INVENTION

In accordance with the invention, a liquid concentrate comprises between about 4 and about 25 wt of an isothiazolinone compound, between about 25 and about 88 wt % of a plasticizer(s) in which said isothiazolinone compound is soluble, and between about 8 and about 50 wt % of benzyl alcohol. The benzyl alcohol stabilizes the concentrate against crystallization and/or freezing at sub-freezing conditions.

Preferably, a concentrate contains at least about 10 wt % DCOIT and at least about 15 wt % benzyl alcohol and, under certain circumstances, preferably at least about 15 wt % DCOIT and at least about 40 wt % benzyl alcohol.

DETAILED DESCRIPTION OF CERTAIN PREFERRED EMBODIMENTS

Generally any plasticizer in which DCOIT is soluble is suitable for forming a concentrate in accordance with the present invention. Examples of such plasticizers include, but are not limited to tricresyl phosphate, dipropylene glycol dibenzoate, diphenylcresyl phosphate, dipropylene glycol dibenzoate, diphenylcresyl phosphate, epoxidized soya, epoxidized tallate, dioctyl azelate, di(2-ethyl hexyl) phthalate, alkyl aryl phosphates, diisobutyl phthalate, diisodecyl phthalate (DIDP), hydrogenated methyl rosin ester, n-octyl n-decyl phthalate, mixed n-alkyl phthalates, butyl benzyl phthalate, di-n-octyl phthalate, di-n-decyl phthalate, 3,4-epoxycyclohexyl methyl 3,4-epoxycyclohexane carboxylate, trioctyl trimellitate and low molecular weight polymeric plasticizers such as Paraplex® G-30 plasticizer sold by Rohm & Haas Co. and the like. Of these plasticizers, di(2-ethyl hexyl) phthalate, diisodecyl phthalate, butyl benzyl phthalate and epoxidized soya are preferred.

The freezing/crystallization problem with DCOIT occurs because DCOIT is solid at room temperature, having a melting point of above 40° C. This compound, exhibits improved stability (weatherability) relative to other isothiazolinone compounds heretofore used as biocides, such as liquid 2-(n-octyl-4-isothiazolin-3-one), in outdoor conditions. Thus, the desire to provide concentrates of this compound.

The invention will now be described in greater detail by way of specific example.

EXAMPLE 1

The following example compares the equilibrium solubility at −10° C. of benzyl alcohol with isodecyl alcohol, a co-solvent which would otherwise be acceptable from environmental and safety standpoints.

| Benzyl alcohol | Isodecyl Alcohol | DIDP | DCOIT |
|---|---|---|---|
| 0.0 | 0.0 | 94.8 | 5.2 |
| 5.8 |  | 86.6 | 7.6 |
| 11.3 |  | 79.9 | 9.6 |
| 21.9 |  | 65.8 | 12.3 |
| 42.3 |  | 42.3 | 15.4 |
|  | 5.9 | 87.8 | 6.4 |
|  | 11.6 | 81.1 | 7.4 |
|  | 23.1 | 69.4 | 7.5 |
|  | 46.8 | 46.8 | 6.5 |

What is claimed is:

1. A liquid concentrate comprising a homogeneous solution of between about 4 and about 25 wt % of 4,5-dichloro-2-(n-octyl-4-isothiazolin-3-one), between about 25 and about 88 wt % of a plasticizer in which said 4,5-dichloro-2-(n-octyl-4-isothiazolin-3-one) is soluble and between about 8 and about 50 wt % of benzyl alcohol.

2. A solution according to claim 1 comprising at least about 10 wt % 4,5-dichloro-2-(n-octyl-4-isothiazolin-3-one) and at least about 15 wt % benzyl alcohol.

3. A solution according to claim 1 comprising at least about 15 wt % 4,5-dichloro-2-(n-octyl-4-isothiazolin-3-one) and at least about 40 wt % benzyl alcohol.

4. The solution according to claim 1 wherein said plasticizer is di(2-ethyl hexyl) phthalate.

5. The solution according to claim 1 wherein said plasticizer is diisodecyl phthalate.

6. The solution according to claim 1 wherein said plasticizer is butyl benzyl phthalate.

7. The solution according to claim 1 wherein said plasticizer is epoxidized soya.

* * * * *